United States Patent [19]

Möller et al.

[11] Patent Number: 5,250,418
[45] Date of Patent: Oct. 5, 1993

[54] PROCESS AND REAGENT FOR DETERMINING THE ACTIVITY OF CHYMOTRYPSIN AND TRYPSIN IN FECES

[75] Inventors: Gerald Möller; Klaus P. Kaspar, both of Tutzing, Fed. Rep. of Germany

[73] Assignee: Boehringer Mannheim GmbH, Mannheim-Waldhof, Fed. Rep. of Germany

[21] Appl. No.: 852,887

[22] Filed: Mar. 17, 1992

Related U.S. Application Data

[63] Continuation of Ser. No. 236,510, Aug. 24, 1988, abandoned, which is a continuation of Ser. No. 431,988, Sep. 30, 1982, abandoned.

[30] Foreign Application Priority Data

Oct. 6, 1981 [DE] Fed. Rep. of Germany ....... 3139719

[51] Int. Cl.[5] .................... C12Q 1/37; C12Q 1/00; G01N 30/00
[52] U.S. Cl. ................................. 435/23; 435/24; 435/4; 435/803; 435/188; 436/174; 436/177
[58] Field of Search .............. 435/4, 18, 23, 24, 803, 435/810, 188; 436/8, 71, 174, 177

[56] References Cited

U.S. PATENT DOCUMENTS 4,282,001 8/1981 Klose et al. ................. 23/230 B

OTHER PUBLICATIONS

Haverback, B., et al. "Measurement of Trypsin and Chymotrypsin in Stool", *Gastroenterology*, 44, pp. 588–597 (1963).
Del Mar, E. G., et al., "A Sensitive New Substrate for Chymotrypsin," *Analytical Biochemistry*, 99, pp. 316–320 (1979).
Kaspar, P., et al., "A New Photometric Method for the Determination of Chymotrypsin in stool," *Fresenius Z Anal Chem*, 311 (1982) 391–92.
Goldberg, D. M., et al., "Binding of trypsin and chymotrypsin by human intestinal mucosa," *Biochim. Biophys. Acta.*, 167, pp. 613–615 (1968).
Remtulla et al., "Is Chymotrypsin Output a Better Diagnostic Index than the Measurement of Chymotrypsin in Random Stool?", *Enzyme 39*, 190-8 (1988).
Goldberg et al.; "Fate of Trypsin and Chymotrypsin in the Human Small Intestine", *Gut 10*, 477–83 (1969).
Kaspar et al., "New Photometric Assay for Chymotrypsin in Stool," *Clin. Chem.* 30, 1753-7 (1984).
Kaspar et al., "The Distribution of Chymotripsin within the Feces and Description of a New Device for the Preparation of Stool Samples", *Clin. Chem.* 30, 1864-6 (1984).
Remtulla et al., "Stool Chymotrypsin Activity Measured by a Spectrophotometric Procedure to Identify Pancreatic Disease in Infants", *Clin. Biochem.* 19, 341–7 (1986).
Durie et al., "Biochemical Tests of Pancreatic Function in Infancy and Childhood", *Adv. Clin. Enzymol.* 4, 77–92 (1986).

*Primary Examiner*—Esther L. Kepplinger
*Assistant Examiner*—Toni R. Scheiner
*Attorney, Agent, or Firm*—Felfe & Lynch

[57] ABSTRACT

The present invention provides a process for the determination of the activity of chymotrypsin or trypsin in feces by measurement of the rate of fission of an appropriate substrate by a fecal suspension in an aqueous or aqueous-organic medium, wherein a fecal sample is suspended in the presence of a surface-active agent.

The present invention also provides a reagent for carrying out this process, comprising a surface-active agent, an enzyme substrate and an aqueous salt solution, said reagent having a pH value of from 7 to 11.

15 Claims, No Drawings

PROCESS AND REAGENT FOR DETERMINING THE ACTIVITY OF CHYMOTRYPSIN AND TRYPSIN IN FECES

This is a continuation of application Ser. No. 07/236,510 filed on Aug. 24, 1988, now abandoned, which is a continuation of application Ser. No. 06,431,988 filed on Sep. 30, 1982, now abandoned.

The present invention is concerned with a process and a reagent for the determination of the activity of chymotrypsin and trypsin in feces.

In the case of a suspicion of chronic pancreatitis and also of mucoviscidosis in neonates, the diagnosis of pancreatic insufficiency is an important parameter, the clinical-chemical detection of which has hitherto not been satisfactorily accomplished. The most dependable test for this purpose is generally regarded as being the pancreozymin secretin test. In this case, after stimulation by pancreozymin and secretin, the pancreatic secretion is collected by means of a probe and subsequently investigated for the following parameters: volume, bicarbonate concentration and the activities of amylase, lipase, trypsin and chymotrypsin. The chief disadvantage of these methods is the large amount of time and technical expense, as well as the great degree of discomfort for the patients.

Another method, not only as an investigating test but also for monitoring control in cases of chronic pancreatitis and of mucoviscidosis is the determination of chymotrypsin and trypsin in the feces. In cases of chronic pancreatitis and of mucoviscidosis, the activity values of trypsin and chymotrypsin are lowered, the chymotrypsin values thereby having proved to be the better parameter. For the determination of chymotrypsin or trypsin in feces, a fecal suspension is mixed with an aqueous methanolic solution of a specific substrate and the amino acid liberated in a given period of time is determined. The determination of the liberated amino acid can be carried out, for example, by titration with an aqueous lye, especially an aqueous solution of sodium hydroxide (pH-stat process, Haverback et al., Gastroenterology, 44, 588–597/1963; Ammann, Fortschritte in der Pankreasfunktionsdiagnostik, pub. Springer Verlag, Berlin, Heidelberg, N.Y., 1967) or the time is measured which leads to the lowering of the pH value of the solution by 0.1 unit (pH-drop process, cf. Robinson, Smith and Elliott, Clin. Chim. Acta., 62, 225–229/1975).

However, all known methods for the determination of the activity of chymotrypsin or trypsin in feces possess the disadvantage of a high expenditure of apparatus and time. A rapid and simple determination of the activity by photometric means has hitherto not been possible: for a reasonably exact determination in the case of the use of a very small sample, the measurement values to be determined are too small and, in the case of a larger sample, the inherent color and turbidity thereof due to suspension particles is too great. A photometric determination after centrifuging the fecal suspension is not possible because the enzyme is bound relatively firmly to the fecal particles and, after centrifuging, is to be found almost completely in the sediment or is only present incompletely and in a non-reproducible amount in solution.

Therefore, it is an object of the present invention to provide a process for the rapid, simple, exact and readily reproducible determination of the activity of chymotrypsin or trypsin in feces.

DESCRIPTION

Thus, according to the present invention, there is provided a process for the determination of the activity of chymotrypsin or trypsin in feces by measurement of the rate of fission of an appropriate substrate by a fecal sample in an aqueous or aqueous-organic medium, wherein a fecal sample is suspended in the presence of a surface-active agent.

The measurement of the rate of fission of the substrate can take place by one of the methods known from the literature, for example by titration of the liberated amino acid by means of a lye (pH-stat process).

We have found that when carrying out the process according to the present invention in the presence of a surface-active agent, in general more than 90% of the enzyme activity is solubilized, the rate of reaction of the substrate fission is considerably increased and the apparent Km value of the substrate is lowered (activation factor about 2 to 10), the problems which have previously arisen (especially binding of the enzyme to the fecal particles and surprisingly high Km values for untreated fecal samples in comparison with crystalline enzyme in the case of particular substrates) thereby being overcome. In particular, it is also possible to measure the fission of the substrate by photometric means quickly, simply, exactly and with the use of only a small amount of substrate. The results obtained with the process according to the present invention in the presence of a surface-active agent are especially surprising because, in the case of pure α-chymotrypsin from bovine pancreas, practically no difference can be ascertained when carrying out the determination with or without the use of a surface-active agent.

The surface-active agent used can, in principle, be any appropriate tenside, such as an anionic or ampholytic tenside and preferably a non-ionic tenside and especially a cationic tenside.

Anionic tensides which can be used include alkanesulphonates, olefin-sulphonates, for example cumenesulphonate, ester sulphonates, alkylarylsul-phonates of the dodecylbenzenesulphonate type, alkylnaphthalenesulphonates, alkyl sulphates, for example sodium lauryl sulphate, ether sulphates and fatty alcohol sulphates and salts of fatty acids and of bile acids; ampholytic tensides are those with anion-active and cation-active hydrophilic groups, for example glycerol derivatives with a betaine structure, sulphobetaines and lecithins; non-ionic tensides include, for example, polyethers, especially alkylphenol polyglycol ethers and other ethoxylation products of fatty acids, fatty acid amides, fatty amines and fatty alcohols, for example ethoxylated lauryl alcohol, polymers of propylene and ethylene oxide, polyoxyethylene alkyl ethers and nonylphenyl ethers, polyoxyethylene sorbitan mondoleate and laurate, addition products of propylene oxide/ethylenediamine/ethylene oxide, amine oxides and fatty acid esters of polyalcohols, tallow alcohol polyglycol ethers; cationic tensides include, for example, straight-chained and cyclic ammonium compounds, for example N-cetyl-N-ethyl-morpholine methosulphate, benzalkonium chlorides and other quaternary ammonium salts, amine salts, pyridinium salts and quaternary fatty amine polyglycol ethers.

The choice of the most appropriate tenside also depends upon the other reaction conditions, especially upon the nature of the enzyme and substrate, upon the nature and concentration of the salts and also upon the pH value of the medium.

Of the cationic detergents, which are especially preferred for the process according to the present invention, the strongest activation effect is displayed by quaternary ammonium compounds and preferably those of the general formula $R_1R_2\ominus N(CH_3)_2$, wherein $R_1$ is preferably an alkyl radical containing 8 to 14 carbon atoms and especially a lauryl or cetyl radical and $R_2$ is preferably a lower alkyl radical containing up to 5 carbon atoms or an aralkyl radical or also a hydroxyalkyl radical and especially a benzyl or methyl radical; and alkylpyridinium salts with preferably 12 to 18 carbon atoms in the alkyl radical, for example lauryl pyridinium chloride, lauryl pyridinium disulphate and especially hexadecyl pyridinium chloride. A tenside which is especially preferred for the process according to the present invention is lauryl trimethyl ammonium chloride.

The concentration of the surface-active agent in the homogenizing solution used for the suspension of the feces is, in general, about 0.02 to about 10% by weight and preferably 0.5 to 5% by weight. The concentration of the surface-active agent in the measurement solution (fecal suspension and substrate solution) should preferably be about 0 0005 to 0.5 and more preferably 0.01 to 0.3% by weight. The concentration of the fecal sample in the suspension is, for example, 0.2 to 2% when using Succ-Ala-Ala-Pro Phe-pNA as substrate.

In addition to the surface-active agent, the homogenizing solution used for the suspension of the feces preferably also contains one or more water-soluble salts, for example alkali metal and/or alkaline earth metal chlorides or sulphates. A content of sodium chloride of 100 to 1000 mmole/liter or a content of calcium chloride of 20 to 500 mmole/liter or a combination of both salts in the given concentration ranges has proved to be especially useful. However, organic salts can also be used, for example acetates or citrates, as well as salts of other cations. The salts are preferably present in a concentration which corresponds to an ionic strength of 20 to 1000.mval/liter Surprisingly, we have ascertained that by means of a homogenizing solution containing a surface-active agent and salts (ionic strength), a superadditive increase of the enzyme activity (increase of the rate of reaction) takes place, i.e. the increase is greater than the sum of the values obtained in the presence of surface-active agent alone or in the presence of salts alone. Furthermore, only the combination of salt and detergent, in contradistinction to the individual components, gives a constantly high and representative portion of the particle-bound enzyme in solution.

As substrate, there can, in general, be used all appropriate substrates known for the determination of the activity of chymotrypsin or trypsin in feces by previously known methods (cf. for example, Grossman, Proc. Soc. Biol. Med., 110, 41/1962, Del Mar et al., Anal. Biochem., 99, 316/1979; Nakajama et al., J. Biol. Chem., 254(10), 4027–4032/1979). Especially preferred for the determination of chymotrypsin, particularly with regard to water-solubility, stability, Km value and velocity constants, is Ala-Ala-Phe-pNA and especially Succ-Ala-Ala-Pro-Phe-pNA and MeO-Succ-Arg-Pro-Tyr-pNA; these substrates are particularly useful for photometric determinations. A substrate which is especially preferred for the determination of trypsin activity is, for example, Chromozyme TRY ® (carbobenzoxyvalyl-glycyl-arginine-p-nitroanilide acetate).

For the preparation of the reagent solution, the substrate is dissolved in water or in a mixture of water and an organic solvent. The organic solvent thereby serves as a solubilizer for the substrate and can be, for example, acetonitrile, dimethylsulphoxide, acetone or methanol. The reagent solution preferably also contains the same salts as are used for the homogenizing solution; the concentration of these salts in the reagent solution is, in general, lower than the concentration in the homogenizing solution; the total salt concentration is preferably about 10 to 500 mmole/liter, for example 250 mmole/liter of sodium chloride and 20 mmole/liter of calcium chloride.

For carrying out the measurement, a definite amount of a suspension of a fecal sample in the homogenizing solution or of the supernatant solution obtained by centrifuging until clear is added to a definite amount of the reagent solution (for example 100 μl. of sample suspension to 2 ml. of reagent solution) and the rate of fission is determined, for example titrimetrically or photometrically. The amount of sample suspension (sample dilution) for the achievement of readily measurable values, for example readily measurable extinction increase/minute, thereby depends especially upon the enzyme activity to be expected. On the basis of the increase of sensitivity by means of the use of the detergent, the amount of sample used can be so small that the inherent absorption of the suspended solid bodies is low and thus a photometric measurement with the suspension only then becomes possible. The pH value of the homogenizing solution is not especially critical; in general, it is from 3 to 10 and preferably from 6 to 8. The pH value of the mixture of sample suspension and reagent solution is generally from 8 to 10 and preferably 9; these values are preferably adjusted via the pH value of the reagent solution It can also be advantageous to add to the solutions, for the adjustment of the pH value, an appropriate buffer mixture, for example tris buffer, glycine buffer or glycylglycine buffer In general, the buffer concentration is from 10 to 1000 mmole/liter and especially 50 to 200 mmole/liter.

If only very small amounts of chymotrypsin are present, such as occur, for example, when measuring devices are used which only permit the picking up of the amount of chymotrypsin present in a surface area, then it is expedient to employ an especially sensitive detection reaction. Such a sensitive reaction is described, for example, in J. Biol. Chem., 128, 537/1939 and is known as the Bratton/Marshall reaction. It depends upon the addition of sodium nitrite and N-α-naphthylethylenediamine and the subsequent addition of acid. The acid used is preferably trichloroacetic acid or an acid of comparable strength.

The measurement can be carried out manually or with an automatic analysis apparatus. For the photometric determination of activity and especially for the automatic photometric measurement (determination of the extinction), it is preferable to centrifuge the sample suspension until clear before carrying out the measurement.

The device described in Federal Republic of Germany Patent Specification No. 31 39 702.6 entitled "Vessel for handling pasty sample material" has proved to be especially useful for carrying out the process according to the present invention. With the process according to the present invention, a simple and aesthetic sampling, sample measurement, working up and measurement of enzyme activity is possible, without discomfort either to the patient or to the laboratory personnel.

The present invention also provides a reagent for carrying out the process, which comprises a surface-active agent, an enzyme substrate and an aqueous salt solution, the reagent having a pH value of from 7 to 11.

A preferred reagent according to the present invention contains the following components:
0.02 to 10% by weight surface-active agent,
0.05 to 5 mmole/liter enzyme substrate,
20 to 1000 mval/liter of a water-soluble salt and
10 to 1000 mmole/liter of a buffer (pH 7 to 11).

A more preferred reagent according to the present invention contains the following components:
0.5 to 5% by weight of surface-active agent,
0.2 to 2 mmole/liter of substrate,
100 to 1000 mmole/liter of sodium chloride and/or
20 to 500 mmole/liter of calcium chloride and
50 to 200 mmole/liter tris buffer (pH 8 to 10).

The following Examples are given for the purpose of illustrating the present invention; if not stated otherwise, the percentages are by weight:

Example 1 a) Preparation of a Homogenizing Solution

| | |
|---|---|
| sodium chloride | 2.9 g. (500 mmole/l.) |
| calcium chloride | 1.1 g. (100 mmole/l.) |
| 33% lauryl trimethyl ammonium chloride | 2.0 g. (0,7%) |
| distilled water | ad 100 ml. | b) Preparation of a Reagent Solution

| | |
|---|---|
| Succ—Ala—Ala—Pro—Phe—pNA | 29.5 mg. (0.5 mmole/l.) |
| sodium chloride | 1.46 g. (250 mmole/l.) |
| calcium chloride | 222 mg. (20 mmole/l.) |
| buffer tris/HCl (pH 9.0) (60 mmole/l.) | ad 100 ml. | c) Homogenization of the Sample

About 100 mg. of fecal sample are mixed with a 100 fold amount by weight of homogenization solution and worked up in an appropriate apparatus to give a fine suspension.

d) Carrying Out of the Measurement

Into a 1 cm. measurement cuvette there are pipetted 2 ml. of the reagent solution which is warmed to 25° C. and mixed with 100 µl. of the sample homogenate. After brief mixing, the increase of the extinction/minute is determined at 405 nm. For calculating the enzyme activity/g. of feces, the extinction increase/minute at 405 nm is multiplied by the factor 212.

Example 2

The preparation of the homogenizing solution and of the reagent solution is carried out as in Example 1, as well as the homogenization of the sample. Subsequent to the homogenization, the suspension is centrifuged until the solution is clear. An aliquot is taken from the centrifuge supernatant and the enzyme activity therein is determined either manually as in Example 1 or with the use of an automatic analysis device.

Example 3 a) Preparation of the Homogenizing Solution

An aqueous solution is prepared with the following components:

| | |
|---|---|
| tris/HCl buffer (pH 9.0) | 60 mmole/liter |
| sodium chloride | 250 mmole/liter |
| calcium chloride | 20 mmole/liter |
| lauryl trimethyl ammonium chloride | 0,7% | b) Preparation of the Reagent Solution

The reagent solution is prepared in the manner described in Example 1.

c) Homogenization of the Sample

This is carried out as described in Example 1.

d) Carrying Out of the Measurement

This is also carried out as described in Example 1.

Example 4 (Comparative)

Example 4 corresponds to Example 3 with the sole difference that the homogenizing solution does not contain detergent (lauryl trimethyl ammonium chloride).

The results of a comparative measurement of identical samples with a reagent according to Example 4 and one according to Example 3 are given in the following Table:

| sample No. | without detergent (Example 4) mE/min. | with detergent (Example 3) mE/min. |
|---|---|---|
| 1 | 31 | 181 |
| 2 | 8 | 68 |
| 3 | 6 | 42 |
| 4 | 8 | 68 |
| 5 | 20 | 159 |

Example 5 a) Preparation of the Homogenizing Solution

This is carried out as described in Example 1.

b) Preparation of the Reagent Solution

An aqueous solution is prepared containing the following components:

| | |
|---|---|
| Ala—Ala—Phe-p-nitroanilide | 2 mmole/liter |
| sodium chloride | 250 mmole/liter |
| calcium chloride | 20 mmole/liter |
| tris/HCl buffer (pH 9.0) | 60 mmole/liter | c) Homogenization of the Sample 200 mg. of fecal sample are mixed with 10 ml. homogenizing solution and worked up in an appropriate apparatus to give a fine suspension.

d) Carrying Out of the Measurement 1 ml. of the reagent solution is pipetted into a 1 cm. cuvette, warmed to 25° C. and mixed with 200 µl. of the sample homogenate. After briefly mixing, the increase of the extinction is measured at 405 nm.

Example 6 (Comparative)

Example 6 corresponds to Example 5 with the sole difference that the homogenizing solution does not contain detergent. The results obtained with an identical sample according to Examples 5 and 6 are as follows:

| without detergent (Example 6) mE/min. | with detergent (Example 5) mE/min. |
| --- | --- |
| 31 | 45 |

Example 7 a) Preparation of the Homogenizing Solution

This is carried out as described in Example 1.

b) Preparation of the Reagent Solution

An aqueous solution is prepared with the following components:

| | |
| --- | --- |
| 3-carbomethoxypropionyl-L-arginyl-L-prolyl-L-tyrosine p-nitroanilide hydrochloride | 0.5 mmole/liter |
| sodium chloride | 250 mmole/liter |
| calcium chloride | 20 mmole/liter |
| tris/HCl buffer (pH 9.0) | 60 mmole/liter | c) Homogenization and measurement take place in the manner described in Example 1.

Example 8 (Comparative)

Example 8 corresponds to Example 7 with the sole difference that the homogenizing solution does not contain any detergent. The results of the measurement of an identical sample according to Examples 7 and 8 are as follows:

| without detergent (Example 8) mE/min. | with detergent (Example 7) mE/min. |
| --- | --- |
| 19 | 148 |

Example 9

Determination of Trypsin a) Preparation of the Homogenizing Solution

This is carried out as described in Example 1.

b) Preparation of the Reagent Solution

An aqueous solution is prepared containing the following components:

| | |
| --- | --- |
| carbobenzoxy-L-valyl-L-glycyl-L-arginine p-nitroanilide acetate | 5 mmole/liter |
| sodium chloride | 250 mmole/liter |
| calcium chloride | 20 mmole/liter |
| tris/HCl buffer (pH 9.0) | 60 mmole/liter | c) Homogenization and d) measurement take place in the manner described in Example 1.

Example 10 (Comparative)

Example 10 corresponds to Example 9 with the sole difference that the homogenization solution does not contain any detergent. The results of the measurement with an identical sample according to Examples 9 and 10 are as follows:

| without detergent (Example 10) mE/min. | with detergent (Example 9) mE/min. |
| --- | --- |
| about 3 | 8 |

Example 11

An aliquot of a fecal sample is measured by means of an appropriate device in such a manner that the sample is present in a chamber which is bounded on one side by a filter paper or the like. For this purpose, there can be used, for example, various commercially available devices for the determination of blood in feces, such as Hemo FEC ® or Feca-Nost ®, after exchange of the appropriate filter paper.

The filter paper is sprinkled with 50 µl. of an aqueous solubilizing solution consisting of:

| | |
| --- | --- |
| lauryl trimethyl ammonium chloride | 50 g./liter (5%) |
| sodium chloride | 500 mmole/liter |
| calcium chloride | 100 mmole/liter | the chymotrypsin of a boundary surface thereby being solubilized and taken up by the filter paper. Subsequently, the filter paper is sprinkled with 50 µl. of a reagent solution of the following composition:

| | |
| --- | --- |
| Succ—Ala—Ala—Pro—Phe-pNA | 2 mmole/liter |
| N-α-naphthylethylenediamine | 5 g./liter |
| sodium nitrite | 1 g./liter |
| tris/HCl buffer (pH 9.0) | 100 mmole/liter |

After a reaction time of 5 minutes, a drop of trichloroacetic acid (3.2 mmole/liter) is applied to the paper. When chymotrypsin is present in the sample, an intense violet coloration is formed, the extent of which depends upon the amount of enzyme.

Example 12 (Comparative)

Example 11 is repeated but with the sole difference that the solution used for the solubilization of the enzyme does not contain any detergent. No visible coloration develops.

It will be understood that the specification and examples are illustrative but not limitative of the present invention and that other embodiments within the spirit and scope of the invention will suggest themselves to those skilled in the art.

What is claimed is:

1. A process for the determination of chymotrypsin or trypsin in a feces sample, comprising the steps of:

suspending the feces sample in an aqueous or aqueous-organic suspension medium including one or more water soluble salts in an amount whereby the ionic strength of the salts from 20 to 1000 mval/liter, and from 0.02% to 10% by weight of a surface-active agent selected from the group consisting of cationic and non-ionic tensides;

contacting the suspended sample with a substrate specific for the determination of chymotrypsin or trypsin by measurement of the rate of fission of the substrate; and photometrically measuring the rate of fission of the substrate as a measure of the activity of chymotrypsin or trypsin in the suspension.

2. The process of claim 1 wherein the surface active agent is a quaternary ammonium salt or an alkyl pyridinium salt.

3. The process of claim 2, wherein the quaternary ammonium salt is lauryl trimethyl ammonium chloride.

4. The process of claims 1 or 2, wherein the concentration of the surface-active agent is 0.5 to 5% by weight.

5. The process of claim 1, wherein the surface-active agent is
   a non-ionic tenside selected from the group consisting of a polyether, a fatty acid amide, a fatty amine, a fatty alcohol, a polymer of propylene and ethylene oxide, a polyoxyethylene sorbitan monooleate or laurate, an addition product of propylene oxide/ethylenediamine/ethylene oxide, an amide oxide or fatty acid ester of polyalcohols and tallow alcohol polyglycol ethers, or
   a cationic tenside selected from the group consisting of a straight-chained or cyclic ammonium compound, a benzalkonium chloride or other quaternary ammonium salt, an amine salt, a pyridinium salt and a quaternary fatty amine polyglycol ether.

6. The process of claim 1, wherein the fission of the substrate forms amino acids, further comprising determining the amino acid formed by the fission.

7. The process of claim 6, wherein the amino acid is determined by titration with a base.

8. The process of claim 1, wherein the water-soluble salt is a sodium salt, a calcium salt, or a mixture thereof.

9. The process of claim 1, wherein the suspension medium comprises 0.02 to 10% by weight of a surface-active agent, 20 to 1000 mval/liter of a water-soluble salt, 10 to 1000 mmol/liter of a buffer (pH 7 to 11) and 0.05 and to 5 mmol/liter enzyme substrate is used.

10. The process of claim 1, wherein the suspension medium comprises 0.5 to 5% by weight of surface-active agent; 100 to 1100 mmole/liter of sodium chloride, 20 to 500 mmole/liter of calcium chloride, or a mixture of 100 to 1100 mmole/liter of sodium chloride and 20 to 500 mmole/liter of calcium chloride; and 50 to 200 mmole/liter of tris buffer (pH 8 to 10); and 0.2 to 2 mmoles/liter of enzyme substrate are used.

11. The process of claim 1, 31 or 32, wherein chymotrypsin is to be determined.

12. The process of claim 11, wherein the substrate used is Ala-Ala-Phe-pNA, Succ-Ala-Ala-Pro-Phe-pNa or MeO-Succ-Arg-Pro-Tyr-pNA.

13. The process of claim 1, 31 or 32, wherein trypsin is determined.

14. The process of claim 13, wherein the substrate used is carbobenzoxy-Val-Gly-Arg-pNA acetate.

15. The process of claim 1, further comprising centrifuging the suspended sample to remove suspended particles therefrom, the determining of chymotrypsin or trypsin being accomplished on a predetermined portion of the supernatant aqueous medium resulting from the centrifugation.

* * * * *

UNITED STATES PATENT AND TRADEMARK OFFICE
CERTIFICATE OF CORRECTION

PATENT NO. : 5,250,418
DATED : October 5, 1993
INVENTOR(S) : Gerald Möller, et al.

It is certified that error appears in the above-indentified patent and that said Letters Patent is hereby corrected as shown below:

<u>IN THE CLAIMS</u>

Column 10,
Claim 11, line 1: change "31 or 32" to -- 9 or 10 --.

Claim 13, line 1: change "31 or 32" to -- 9 or 10 --.

Signed and Sealed this

Sixth Day of September, 1994

Attest:

BRUCE LEHMAN

*Attesting Officer*     *Commissioner of Patents and Trademarks*